(12) United States Patent
Kim et al.

(10) Patent No.: US 7,959,956 B2
(45) Date of Patent: Jun. 14, 2011

(54) METHOD FOR TREATING DIABETIC COMPLICATIONS

(75) Inventors: Jin Sook Kim, Seoul (KR); Sang Won Lee, Seoul (KR); Yin Mi Lee, Namyangiu-si (KR)

(73) Assignee: Korea Institute of Oriental Medicine, Ltd., Daejeon (KR)

( * ) Notice: Subject to any disclaimer, the term of this patent is extended or adjusted under 35 U.S.C. 154(b) by 203 days.

(21) Appl. No.: 12/257,316

(22) Filed: Oct. 23, 2008

(65) Prior Publication Data

US 2009/0087504 A1     Apr. 2, 2009

Related U.S. Application Data

(62) Division of application No. 10/588,561, filed as application No. PCT/KR2004/003554 on Dec. 31, 2004, now abandoned.

(30) Foreign Application Priority Data

Feb. 6, 2004   (KR) ........................ 10-2004-0008047

(51) Int. Cl.
  *A61K 36/00*   (2006.01)
  *A61K 36/47*   (2006.01)
  *A61K 36/57*   (2006.01)
  *A61K 36/488*  (2006.01)
  *A61K 36/484*  (2006.01)
  *A61K 36/48*   (2006.01)
  *A61K 38/00*   (2006.01)

(52) U.S. Cl. ........ 424/725; 424/773; 424/775; 424/757; 514/6.9

(58) Field of Classification Search ........................ None
  See application file for complete search history.

(56) References Cited

U.S. PATENT DOCUMENTS

| 6,093,403 | A | * | 7/2000 | Huo et al. ................. 424/195.15 |
| 2002/0146404 | A1 | | 10/2002 | Tsuji et al. |
| 2003/0194451 | A1 | | 10/2003 | Cho et al. |

FOREIGN PATENT DOCUMENTS

| CN | 1151306 A | 6/1997 |
| CN | 1164401 A | 11/1997 |
| CN | 1273843 A | 11/2000 |
| CN | 1341441 A | 3/2002 |

OTHER PUBLICATIONS

Kim et al, Studies on the processing of herbal medicines (III)-HPLC analysis of magnolol and inhibitory effects on the formation of advanced glycation end products (AGEs) in vitro of unprocessed- and processed Magnolia Bark, Korean Journal of Pharmacognosy (2002) 33 (4): 308-311.*
Duan et al, Inhibitory effects of Radix puerariae on nonenzymic glycosylation of proteins, Shenyang Yaoke Daxue Xuebao (2000), 17 (1), 61-62.*
Alarcon-Aguilara et al, Study of the anti-hyperglycemic effect of plants used as antidiabetics, Journal of Ethnopharmacology 61 (1998) 101-110.*
Bang, H.K., et al., Arch. Pharm., Res., 23:46-49 (2000).
Brownlee, M., et al., Sciences, 232, 1629-1632 (1986).
Soulis-Liparota, T., et al., Diabetologia, 38: 387-394 (1995).
Edelstein, D., et al., Diabetes, 41 26-29 (1992).
Kim, J.G., et al., Yakhak Hoeji, 40, 170-176, 1996.
Kim, H., Chinese medicinal pharmacology, Jiipmoondang, 92-94 (2001).
Komoshima, T., et al., J. Nat. Prod., 54: 816-822 (1991).
Kuribara, H., et al., J. Pharm. Pharmacol., 51: 97-103 (1999).
Lee, et al., Biochem. Biophys. Res. Comm., 123: 888 (1984).
Monnier, et al., Proc. Natl. Acad. Sci. USA, 81:583 (1984).
Shin, M.K., Clinical Botany with Original Colors, Youngryumsa, 487, (1996).
Shin, T.Y., et al., Arch. Pharm., Res., 24: 249-255 {2001).
Smith, P.R., et al., Eur. J. Biochemistry, 210: 729-739 (1992).
Son, H.J., et al., Planata med., 66:467-471, 2000.
Vinson, J.A., et al., Journal of Nutritional Biochemistry 7: 559-663 (1996).
Simpson et al., The prevention of type 2 diabetes-lifestyle change or pharmacotherapy? A challenge for the 21$^{st}$ century. Diabetes Research and Clinical Practice 59 (2003) 165-180.

* cited by examiner

*Primary Examiner* — Qiuwen Mi
(74) *Attorney, Agent, or Firm* — Birch, Stewart, Kolasch & Birch, LLP (57) ABSTRACT

The present invention relates to a method for treating diabetic complications, which comprises administering an extract obtained by: crashing and drying any one selected from Euphorbiae radix, gingered *Magnolia* bark, parched Puerariae radix and Glycyrrhizae radix; extracting the dried herbal material with alcohol or aqueous alcohol solution; filtering the extract; and concentrating the filtrate under reduced pressure.

3 Claims, 7 Drawing Sheets

NORMAL GROUP

DIABETES-INDUCED GROUP ADMINISTERED
WITH HERBAL EXTRACT MIXTURE

DIABETES-INDUCED GROUP

FIG. 10

NORMAL GROUP

DIABETES-INDUCED GROUP ADMINISTERED
WITH HERBAL EXTRACT MIXTURE

DIABETES-INDUCED GROUP

FIG. 11

NORMAL GROUP

DIABETES-INDUCED GROUP ADMINISTERED WITH HERBAL EXTRACT MIXTURE

DIABETES-INDUCED GROUP ature, resulting in chronic diabetic
METHOD FOR TREATING DIABETIC COMPLICATIONS This application is a Divisional of application Ser. No. 10/588,561 filed on Aug. 4, 2006 (now abandoned), and for which priority is claimed under 35 U.S.C. §120; application Ser. No. 10/588,561 is the National Phase of PCT International Application No. PCT/KR2004/003554 filed on Dec. 31, 2004 under 35 U.S.C. §371. This Application also claims priority to Application No. 10-2004-0008047 filed on Feb. 6, 2004 in Korea under 35 U.S.C. §119(a). The entire contents of each of the above-identified applications are incorporated by reference.

TECHNICAL FIELD

The present invention relates to a composition for the prevention and treatment of diabetic complications. More particularly, the present invention relates to a pharmaceutical composition and functional food effective for inhibiting the production of advanced glycation endproducts (ACEs) to prevent and treat diabetic complications, which contains an extract from each of Euphorbiae radix, gingered *Magnolia* bark, parched Puerariae radix and Glycyrrhizae radix, or a mixture of extracts from these herbal materials, or magnolol isolated from *Magnolia* bark, thus inhibiting the production of advanced glycation endproducts (ACEs).

BACKGROUND ART

Diabetes is one of important adult diseases all over the world, and in Korea, it reaches a prevalence rate of 7-8% with rapid economic growth and becomes an important cause of death of people in the 60-70-year-old age group. Diabetic complication, a cause of death by diabetes, occurs by the damage of almost all organs in the body at 10-20 years after the onset of diabetes, and is expressed as diabetic retinopathy, diabetic cataract, diabetic nephropathy, diabetic neuropathy, etc. Particularly, chronic diabetic nephropathy is the most important cause of end-stage renal disease and cannot be treated by other therapies than blood dialysis therapy and organ transplantation. This diabetic complication can progress even when diabetes is cured so as to recover the normal blood glucose concentration. This diabetic complication is known to be caused mainly by advanced glycation endproducts (AGEs) irreversibly produced as a result of the nonenzymatic glycation of protein due to the continuation of a high blood glucose condition.

Mechanisms of causing this diabetic complication are broadly described as the nonenzymatic glycation of protein, polyol pathways, oxidative stress, etc.

The nonenzymatic glycation of protein is caused by the nonenzymatic condensation of the amino acid groups (e.g., lysine residues) of protein with glucose, which produces advanced glycation endproducts (AGEs). The nonenzymatic glycation of protein can consist of the following two steps: (1) the amino acid groups (e.g., lysine residues) of protein, and the aldehydes or ketones of glucose, are subjected to nucleophilic addition reaction without the action of enzymes so as to form Schiff bases as early-stage products, and ketoamine adducts adjacent to the Schiff bases are condensed with each other to produce reversible Amadori-type early glycation products; and (2) by the continuation of a high blood glucose condition, the reversible Amadori-type early glycation products are rearranged without degradation and cross-linked with proteins, thus producing advanced glycation endproducts.

Unlike the reversible Amadori-type early glycation products, the advanced glycation endproducts are irreversible. Thus, even when blood glucose is recovered to a normal level, the endproducts, once produced, are accumulated in tissues during a protein existing period without degradation, resulting in an abnormal change in the structure and function of the tissues (Vinson, J. A. et al., 1996, *J. Nutritional Biochemistry* 7: 559-663; Smith, P. R. et al., 1992, *Eur. J. Biochem.*, 210: 729-739).

For example, glycated albumin, one of advanced glycation endproducts produced by the reaction of glucose with various proteins, acts as an important factor of causing chronic diabetic nephropathy. The glycated albumin is introduced into glomerular cells more easily than non-glycated normal albumin, and a high concentration of glucose stimulates glomerular cells to increase the synthesis of extracellular matrices. The excessive introduction of glycated albumins and the increase of extracellular matrices result in the fibrillation of glomerules. By such mechanisms, the glomerules are continuously damaged, eventually making the use of an extreme treatment method, such as blood dialysis or organ transplantation, unavoidable. Also, it was reported that, due to chronic diabetes, collagens are accumulated on the arterial wall, and basement membrane proteins are accumulated on glomerules by binding to advanced glycation endproducts (Brownlee, M., et al., 1986, *Sciences*, 232, 1629-1632).

As described above, the nonenzymatic protein glycation leads to the glycation of basement membranes, serum albumins, lens proteins, fibrins, collagens, etc., and the advanced glycation endproducts cause an abnormal change in the structure and function of the tissues, resulting in chronic diabetic complications, such as diabetic retinopathy, diabetic cataract, diabetic nephropathy, diabetic neuropathy, etc.

Moreover, it is known that the advanced glycation endproducts produced in the nonenzymatic protein glycation also play an important role in aging (Monnier et al., Proc. Natl. Acad. Sci. USA, 81: 583, 1984; Lee et al., Biochem. Biophys. Res. Comm., 123: 888, 1984; Diabetologia, 38: 357-394).

As described above, the advanced glycation endproducts produced in the nonenzymatic protein glycation are main factors in the progression of diabetic complication and aging. Thus, to prevent the progression of diabetic complication and aging, the production of advanced glycation endproducts need to be inhibited.

Currently, the only synthetic drug as a protein glycosylation inhibitor is aminoguanidine, a nucleophilic hydrazine, which prevents Amadori products from crosslinking with proteins, by binding to the Amadori products, so as to inhibit the production of advanced glycation products, thus delaying or preventing the development of diabetic complication (Brownlee, M., et al., 1986, Sciences, 232, 1629-1632; Edelstein, D. et al., 1992, Diabetes, 41, 26-29). The aminoguanidine, which is the most promising synthetic drug candidate for the prevention and treatment of diabetic complication, was developed up to third-phase clinical trials but has the problem of causing toxicity upon long-term administration. Thus, the development of safer drugs is now needed.

Accordingly, due to limitations in disease-treating agents with the existing synthetic compounds and the problems of side-effects and toxicity in the application of such treating agents, the development of disease-treating agents based on medicinal herbal formulations are now actively conducted.

Thus, during studies on medicinal herbal materials for the prevention and treatment of diabetic complication and aging, the present inventors have found that Euphorbiae radix, gingered *Magnolia* bark, parched Puerariae radix and Glycyrrhizae radix are effective for inhibiting the production of advanced glycation endproducts, and particularly, a mixture consisting of these herbal materials at an amount of each herbal material of 5-85% by weight based on the total weight of the herbal materials taken as 100% by weight, and magnolol isolated from *Magnolia* bark, have an excellent effect on the inhibition of production of advanced glycation endproducts and thus, are useful for not only the prevention and treatment of diabetic complication but also the prevention and delay of aging. On the basis of these findings, the present invention has been completed.

DISCLOSURE OF INVENTION

Technical Problem

It is therefore an object of the present invention to provide a composition for the prevention and treatment of diabetic complication, which contains, as an active ingredient, an extract from any one selected from Euphorbiae Radix, gingered *Magnolia* bark, parched Puerariae radix and Glycyrrhizae radix.

Another object of the present invention is to provide a composition for the prevention and treatment of diabetic complication, which contains, as an active ingredient, a mixture of extracts from Euphorbiae radix, gingered *Magnolia* bark, parched Puerariae radix and Glycyrrhizae radix.

Still another object of the present invention is to provide a composition for the prevention and treatment of diabetic complication, which contains, as an active ingredient, an extract from a mixture of Euphorbiae Radix, gingered *Magnolia* bark, parched Puerariae radix and Glycyrrhizae radix.

Still another object of the present invention is to provide a composition for the prevention and treatment of diabetic complication, which contains, as an active ingredient, magnolol isolated from *Magnolia* bark, or a pharmaceutically acceptable salt thereof.

Still another object of the present invention is to provide a pharmaceutical composition for the prevention and treatment of diabetic complication, which contains, as active ingredients, said single herbal extract, said herbal extract mixture, or said isolated magnolol.

Still another object of the present invention is to provide a functional food for the prevention and treatment of diabetic complication, which contains, as active ingredients, said single herbal extract, said herbal extract mixture, or said isolated magnolol.

Still another object of the present invention is to provide a pharmaceutical composition for the prevention and delay of aging, which contains, as active ingredients, said each single herbal extract, said herbal extract mixture, or said isolated magnolol.

Still another object of the present invention is to provide a functional food for the prevention and delay of aging, which contains, as active ingredients, said each extract, said medicinal herbal mixture, or said magnolol.

Technical Solution

To achieve the above objects, in one embodiment, the present invention provides a composition which contains an extract obtained by: crushing and drying any one selected from Euphorbiae radix, gingered *Magnolia* bark, parched Puerariae radix and Glycyrrhizae radix; extracting the dried herbal material with alcohol or aqueous herbal solution; filtering the extract; and concentrating the filtrate under reduced pressure.

In another embodiment, the present invention provides a composition which contains an herbal extract mixture obtained by: crushing and drying each of Euphorbiae Radix, gingered *Magnolia* bark, parched Puerariae radix and Glycyrrhizae radix; mixing the crushed herbal materials together, each of the herbal materials being used at an amount of 5-85% by weight based on the total weight of the herbal materials taken as 100% by weight; extracting the herbal mixture with alcohol or aqueous alcohol solution; filtering the extract; and concentrating the filtrate under reduced pressure.

In still another embodiment, the present invention provides a composition containing extracts from Euphorbiae Radix, gingered *Magnolia* bark, parched Puerariae radix and Glycyrrhizae radix, in which the amount of each of the extracts is 5-85% by weight based on 100% by weight of the mixture of the extracts.

In yet another embodiment, the present invention provides a composition which contains magnolol obtained by: extracting *Magnolia* bark with aqueous 80% ethanol solution at ambient temperature for 24 hours; systematically separating the extract in the order of normal-hexane, ethyl acetate and normal-butanol; separating the normal-hexane layer into pre-fractions by normal silica gel chromatography; comparing the pre-fractions with the standard form magnolol on TLC to determine a magnolol-enriched fraction; and separating magnolol from the magnolol-enriched fraction by silica gel column chromatography.

Hereinafter, the medicinal herbal materials which are used in the present invention will be described.

Euphorbiae radix is the root of *Elphorbia pekinensis*, a perennial herb belonging to Euphorbiaceae, and contains gallic acid, methylgallate, 3-0-galloylshikimic acid, etc. (Kim, J. G., et al., Yakhak Hoeji, 1996, 40, 170-176). It is bitter and pungent in taste, and cold in nature. In the spleen, lungs and stomach, it shows the effects of removing and expelling retained water by hydrogogue and mitigating boils (Min-Kyo, Shin, Clinical Botany with Original Colors, Youngryumsa, 487, 1996).

*Magnolia* bark, which is the dried bark of *Magnolia obovata, M. officinalis* or *M. officinalis* var. *biloba* belonging to Magnoliaceae, has the effects of eliminating dampness and phlegm, and promoting the circulation of "Gi", and thus treating the following symptoms: driving Gi downward; retention of dampness and acupuncture if the diaphragm; numbness in skin and vomiting and diarrhea; retention of undigested food; abdominal distension and constipation; coughing caused by phlegm. (See The State Pharmacopoeia Commission of the People's Republic of China, Pharmacopoeia of the People's Republic of China, Chapter I, 204, Chemistry Industry Pressing, Beijing). Also, *Magnolia* bark contains essential oils, such as $\alpha$, $\beta$, $\gamma$-eudesmol, magnolol, honokiol, alkaloid, saponin, etc. The known pharmacological effects of *Magnolia* bark include anti-allergic effects (Shin, T. Y., et al., 2001, Arch. Pharm., Res., 24: 249-255), apoptotic effects (Park, H. J., et al., 2001, Arch. Pharm., Res., 24: 342-348), NO synthesis-inhibiting effects, TNF-$\alpha$ expression-inhibiting effects (SOn, H. J., et al., 2000, Planata med., 66:467-471), antifungal effects (Bang, K. H., et al., 2000, Arch. Pharm, Res., 23: 46-49), mental health-promoting effects (Kuribara, H., et al, 1999, J. Pharm. Pharmacol., 51: 97-103), and skin cancer-inhibiting effects (Komoshima, T. et al., 1991, J. Nat. Prod., 54: 816-822).

Puerariae radix is the dried root of *Pueraria thunbergiana* (*P. lobata*), a perennial plant belonging to Fabaceae. It is sweet, pungent and ordinary in taste. In the spleen and stomach, it shows the effects of releasing the exterior, eliminating bruised spots, producing the body fluid, and arresting diarrhea. The reported pharmacological actions of Puerariae radix include fever alleviation, blood pressure lowering, memory enhancement, cerebral blood flow increase, coronary artery dilatation, heart function improvement, antiarrhythmic actions and the like (Ho-Chul, Kim, Chinese medicinal pharmacology, JiipMoonDang, 92-94, 2001).

Glycyrrhizae radix is obtained by drying the root and root stem of *Glycyrrhiza glabra, G. uralensis* and others, which are perennial plants belonging to Fabaceae. It is sweet and ordinary in taste. In the spleen, stomach, heart and lungs, it shows the effects of strengthening the spleen and stomach, augmenting "Gi" clearing heat, removing toxicity, moistening the lungs, alleviating and stopping a pain, and regulating "Gi". It mainly contains glycyrrhizin (triterpen saponin), flavonoid compounds, such as liquiritin, and the like. The pharmacological effects of Glycyrrhizae radix include effects similar to those of adrenal cortex hormones, gastric ulceration inhibition, smooth muscle relaxation, liver function protection, anti-inflammation, anti-allergy, and anti-virus effects (Ho-Chul, Kim, Chinese medicinal pharmacology, Jiip-MoonDang 434-436, 2001).

BEST MODE FOR INVENTION

Hereinafter, the present invention will be described in detail.

The inventive composition for the prevention and treatment of diabetic complication contains an extract obtained by the steps of: (1) drying and crushing any one selected from Euphorbiae radix, gingered *Magnolia* bark, parched Puerariae radix and Glycyrrhizae radix, and then extracting the crushed material with alcohol having 1-4 carbon atoms; and (2) filtering the extract obtained in the step (1), and concentrating the filtrate under reduced pressure.

As the alcohol used in the step (1), although 10-90% alcohol having 1-4 carbon atoms can be used, 80% ethanol is preferably used at an amount of 5-10 times (w/v) the herbal medicinal material.

The gingered *Magnolia* bark used in the step (1) is prepared by treating *Magnolia* bark in the following manner. To *Magnolia* bark in a container preheated to 50-100° C., ginger is added at an amount of about 3 parts by weight based on 100 parts by weight of *Magnolia* bark, and water is put in the container at an amount of 5-10 times (w/v) the herbal material such that *Magnolia* bark is completely immersed in water. Then, the herbal material is heated while maintaining a temperature of 70-100° C. When water is almost evaporated, *Magnolia* bark is taken out from the container. The gingered *Magnolia* bark thus obtained shows an increase in inhibitory effect against the production of advanced glycation endproducts as compared to *Magnolia* bark.

Parched Puerariae radix used in the step (1) is prepared by treating Puerariae radix in the following manner. 100 g of Puerariae radix is parched at 120-130° C. for 45 minutes. As the surface of Puerariae radix becomes yellow and shows brown spots, Puerariae radix is taken out and cooled. Parched Puerariae radix thus obtained shows an increase in inhibitory effect against the production of advanced glycation endproducts as compared to Puerariae radix.

Alternatively, the herbal extract mixture according to the present invention is obtained by mixing the extracts of the four herbal materials obtained in the steps (1) and (2), the amount of each of the herbal extracts being 5-85% by weight based on the total weight of the herbal extracts taken as 100% by weight.

Alternatively, the herbal extract mixture according to the present invention is obtained by: crushing and drying each of Euphorbiae radix, gingered *Magnolia* bark, parched Puerariae radix and Glycyrrhizae radix; mixing the crushed herbal materials, each of the herbal materials being used at an amount of 5-85% based on the total weight of the herbal materials taken as 100% by weight; and extracting the herbal mixture in the same manner as in the steps (1) and (2).

In in vitro tests, the inventive single herbal extract and mixed herbal extracts effectively inhibited the production of advanced glycation endproducts which cause diabetic complication. In animal tests, they were excellent in blood glucose-lowering effects and showed an increase in body weight, a reduction in kidney hypertrophy, and remarkable reductions in BUN, triglyceride and creatinine levels, as compared to a diabetes-induced group. This suggests that they recover deteriorated kidney functions. In addition, they showed a remarkable reduction in the opacity of the eye lens as compared to the diabetes-induced group, indicating that they are effective for the delay or prevention of cataract onset.

Also, magnolol according to the present invention is obtained by isolation from *Magnolia* bark, and represented by the formula (I) below.

Although magnolol, the index material of *Magnolia* bark, was known to have an inhibitory effect against histamine release, its inhibitory effect against the production of advanced glycation endproducts was first found in the present invention.

[Formula 1]

A method for isolating magnolol from *Magnolia* bark comprises the steps of:
(1) extracting *Magnolia* bark with 80% ethanol aqueous solution at ambient temperature for 24 hours; (2) systematically separating the extract in the order of n-hexane, ethyl acetate and n-butanol; (3) selecting the n-hexane layer and separating the selected n-hexane layer by normal silica gel (340 g) chromatography (using an n-hexane-ethyl acetate mixture as a mobile phase) into pre-fractions; (4) comparing the pre-fractions with the standard form magnolol on TLC to determine a magnolol-enriched fraction; and (5) isolating magnolol from the magnolol-enriched fraction by normal silica gel chromatography. Magnolol thus isolated is identified by analyses such as nuclear magnetic resonance, mass spectrometry, IR, etc.

The isolated magnolol can be converted into a pharmaceutically acceptable salt according to any conventional method known in the art. For this purpose, pharmaceutically acceptable free acids which can be used in the present invention include inorganic acids and organic acids. Inorganic acids include hydrochloric acid, bromic acid, iodic acid, sulfuric acid and phosphoric acid, and organic acids include citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, 4-toluenesulfonic acid, glutamic acid, and aspartic acid.

It was found that, in in vitro tests, the isolated magnolol inhibited the glycation of bovine serum albumin (BSA) and had the effect of inhibiting the glycation of advanced glycation endproducts.

Accordingly, the inventive single herbal extract, mixed herbal extract and magnolol will be useful for the prevention and treatment of diabetic complications caused by the production of advanced glycation endproducts, for example, diabetic retinopathy, diabetic cataract, diabetic nephropathy, and diabetic neuropathy, etc.

Also, the inventive single herbal extract, mixed herbal extract, and magnolol, inhibit the production of advanced glycation endproducts, resulting in reductions in the production of free radicals and the incidence of oxidative stresses. Thus, they will be useful for the prevention and delay of aging caused by oxidative stress.

The composition containing the inventive single herbal extract, mixed herbal extract or magnolol may additionally contain at least one active ingredient showing the same or similar function as these components.

In clinical administration, the inventive composition containing the single herbal extract or the herbal extract mixture may be administered orally or parenterally, and used as a general drug formulation.

The composition containing the inventive single herbal extract or mixed herbal extract may be administered by various routes at effective amounts. The composition also contains a pharmaceutically acceptable carrier. Any pharmaceutically acceptable carrier may be used if it is the standard pharmaceutical carrier which can be used in known formulations, such as sterilized solutions, tablets, coated tablets, and capsules.

Generally, carriers include excipients, such as starch, milk, sugar, particular clays, gelatin, stearic acid, talc, vegetable oil, gum, glycol, and other known excipients. In addition, sweetening agents, pigment additives, and other components may also be included. The inventive composition containing the inventive single herbal extract or mixed herbal extract as an active ingredient may be administered by various routes including but not limited to, oral, intravenous, intramuscular, transdermal routes, etc. In actual clinical administration, the inventive composition may be administered orally or parenterally in the form of various formulations, and it is formulated with generally used diluents or excipients, such as fillers, vehicles, binders, wettings, disintegrants, surfactants, etc.

Solid formulations for oral administration include tablets, pills, powders, granules, capsules and the like, and these solid formulations are prepared with at least one excipient, such as starch, calcium carbonate, sucrose, lactose, gelatin, etc. In addition to simple excipients, lubricants such as magnesium stearate and talc may also be used.

Liquid formulations for oral administration include suspensions, internal dosage forms, emulsions, syrups, etc., in which case simple diluents, such as water or liquid paraffin, and other various excipients, such as wetting agents, sweetening agents, aromatics, and preservatives, may be used.

Furthermore, the inventive composition may be administered by parenteral routes, such as subcutaneous, intravenous and intramuscular injections. In order to prepare formulations for parenteral administration, the single herbal extract or the mixed herbal extract is mixed with a stabilizer or buffer in water to form a solution or suspension, which is then formulated into unit-dose ampoules or vials.

The dose of the inventive single herbal extract or mixed herbal extract is suitably selected depending on the in vivo absorption, inactivation rate and excretion rate of the active ingredient, the age, sex and condition of patients, and the severity of diseases to be treated. It may be administered 1-3 times daily. The effective dose of the inventive single herbal extract or mixed herbal extract contained in the composition is 500-2,000 mg/kg/day, and preferably 500-1,000 mg/kg/day.

The accurate dose, administration route and number of the inventive formulation can be easily determined depending on the properties of the formulation, the bodyweight and condition of a subject, and the properties of particular derivatives to be used.

In the present invention, the single herbal extract and the mixed herbal extract were tested for acute toxicity on test rats, and the results showed that they had a minimum lethal dose ($LD_{50}$) of at least 6 g/kg, indicating no toxicity. This suggests that the inventive extract has a very high safety in the body. Accordingly, the inventive single herbal extract or mixed herbal extract may be administered safely to the body.

The inventive single herbal extract or mixed herbal extract may be used for the prevention and treatment of diabetic complications and for the prevention and delay of aging, alone or in combination with surgery, radiation therapy, hormonal therapy, chemical therapy, and/or methods using biological regulators.

The inventive single herbal extract or mixed herbal extract may be added to foods for improving diseases caused by diabetic complication and aging. The inventive single herbal extract or mixed herbal extract may be added to foods alone or in combination with other foods or food additives, and suitably used according to a conventional method.

The amount of addition of the active ingredient (herbal extract) can be suitably determined depending on the use purpose (prevention, health promotion or treatment). Generally, in the preparation of foods or drinks, the inventive herbal extract mixture is added at an amount of less than 15% by weight, and preferably 10% by weight, based on 100% of raw materials. However, for the purpose of health and hygiene or in the case of long-term intake for health control, the amount of addition of the inventive extract may be lower than the above-described amount. However, since the extract has no problem in view of safety, the active ingredient may also be used at a higher amount than the above-described amount.

There are no special limitations on the kind of the foods. Examples of foods to which the extract may be added include dairy products, such as meats, sausages, breads, chocolates, candies, snacks, confectioneries, pizzas, noodles, fried noodles, gums and ice creams, various soups, beverages, teas, drinks, alcoholic drinks and vitamin complexes, as well as all foods which are functional in a common sense.

The inventive functional foods may additionally contain various sweetening agents or natural carbohydrates as in conventional beverages. The natural carbohydrates include monosaccharides, such as glucose and fructose, disaccharides, such as maltose and sucrose, polysaccharides, such as dextrin and cyclodextrin, and sugar alcohols, such as xylitol, sorbitol, and erythritol. Sweeteners include natural sweeteners such as thaumatin and stevia extracts, and synthetic sweeteners, such as saccharin and aspartame. The natural carbohydrates are used at an amount of about 0.01-0.04 g, and preferably about 0.02-0.03 g based on 100 ml of the inventive composition.

In addition, the inventive composition may contain various nutrients, vitamins, electrolytes, flavoring agents, colorants, pectic acid or its salt, alginic acid or its salt, organic acids, protective colloidal tackifiers, pH adjusters, stabilizers, preservatives, glycerin, alcohol, carbonating agents used in carbonated drinks, etc. Also, the inventive composition may contain fruit flesh for the preparation of natural fruit juices, fruit juice beverages and vegetable juices. These components may be used alone or in combination. Although not critical, these additives are used at an amount of 0.01-0.1 parts by weight based on 100 parts by weight of the inventive composition.

MODE FOR INVENTION

Hereinafter, the present invention will be described in further detail by the following examples and test examples. It is to be understood, however, that these examples are given for illustrative purpose only and are not construed to limit the scope of the present invention.

Example 1

Preparation of Medicinal Herbal Extract

Euphorbiae radix was powdered, and 100 g of the powder was taken and extracted with 1 liter of 80% ethanol aqueous solution (ethanol:distilled water=80:20) at ambient temperature (20-30° C.) for 24 hours. The ethanol extract was filtered through filter paper, and then, the extraction and filtration steps repeated five times in the same manner as described above. All the extracts were collected and concentrated under reduced pressure.

Meanwhile, Euphorbiae radix, 100 g of each of gingered *Magnolia* bark, parched Puerariae Radix and Glycyrrhizae radix was extracted with 1 liter of 80% ethanol aqueous solution. Each of the extracts was filtered and concentrated under reduced pressure. As a result, obtained were 20 g of the Euphorbiae radix extract, 10 g of the gingered *Magnolia* bark extract, 20 g of the parched Puerariae radix extract, and 20 g of the Glycyrrhizae radix extract.

Example 2

Preparation of Herbal Extract Mixture

The extracts prepared in Example 1 were mixed together at an amount of 10 g for each herbal extract, thus obtaining 40 g of an herbal extract mixture.

Example 3

Another Preparation of Herbal Extract Mixture

Euphorbiae radix, gingered *Magnolia* bark, parched Puerariae radix and Glycyrrhizae radix were powdered, and four kinds of the powers were mixed together at an amount of 100 g for each herbal material. The mixture was extracted with 1 liter of 80% ethanol aqueous solution (ethanol:distilled water 80:20) at ambient temperature (20-30° C.) for 24 hours. The ethanol extract was filtered through filter paper, and then, the extraction and filtration steps were repeated five times in the same manner as described above. All the extracts were collected and concentrated under reduced pressure.

Example 4

Isolation of Magnolol 2 kg of *Magnolia* bark was extracted with 10 liters of 80% ethyl alcohol aqueous solution at ambient temperature for 24 hours, followed by filtration. The extraction and filtration steps were repeated three times, and all the resulting extracts were concentrated under reduced pressure and dried, thus obtaining 250 g (12.5% yield) of a dark-brown extract. This extract was systemically separated in the order of n-hexane, ethyl acetate and n-butanol.

Of the separated layers, the n-hexane layer distributed with magnolol was selected and subjected to normal silica gel (340 g) chromatography, thus yielding pre-fractions. Here, the n-hexane layer was eluted with a mobile phase of n-hexane: ethyl acetate at a gradient of 1:0 to 6:, thus yielding pre-fraction 1 to pre-fraction 6. The pre-fractions were compared with the standard form magnolol and, as a result, the pre-fraction 4 was determined to be rich in magnolol. The pre-fraction was subjected to silica gel chromatography, thus isolating 15 mg of magnolol. It was determined to be magnolol by the results of various analyses, including NMR, mass spectrometry and IR.

Test Example 1

Analysis of Effects of Inventive Single Herbal Extract, Mixed Herbal Extract and Magnolol on Inhibition of Production of Advanced Glycation Endproducts In order to examine the effects of the inventive single herbal extract, mixed herbal extract and magnolol on the inhibition of production of advanced glycation endproducts, the following tests were carried out.

(1) Effect of Inventive Herbal Extract Mixture on Inhibition of Production of Advanced Glycation Endproducts As a protein source, bovine serum albumin (hereinafter, referred to as "BSA"; Sigma, USA) was used. BSA was dissolved in 50 mM phosphate buffer (pH 7.4) to a concentration of 10 mg/ml.

As a sugar source, a mixture of 0.1 M fructose and 0.1 M glucose was used.

This sugar mixture was added to the prepared BSA solution, for use in tests.

The herbal extract mixture prepared in Example 2 was dissolved in 15% Tween80, and this solution was added to the BSA-sugar mixture and cultured at 37° C. for 30 days. At this time, 0.02% sodium azide was used as an antibacterial agent.

As a control group, a culture consisting of BSA and the sugar mixture was cultured, and as blanks to the control and test groups, the materials for the test group and the materials for the control group were used after preparation without incubation.

In order to reduce errors to the lowest possible extent, 4 samples for each group were used. Just before culturing, the samples were filled with nitrogen gas (99.999% purity) in order to prevent them being contaminated. After 30 days, the content of advanced glycation endproducts in the culture media was analyzed. The advanced glycation endproducts are fluorescent, show a brown color, are crosslinkable, and have ligands which can be recognized by cellular membrane receptors. The amount of the advanced glycation endproducts with such properties was measured with a spectrophotometer (excitation at 350 nm and release at 450 nm) so as to determine the inhibition of production of the advanced glycation endproducts.

The inhibition (%) of production of advanced glycation endproducts was calculated according to the following equation:

Inhibition (%) of production=100−[(fluorescent intensity of test group−fluorescent intensity of blank to test group)/(fluorescent intensity of control group−fluorescent intensity of blank to control group)]×100

(2) Effect of Extract from Each of Euphorbiae Radix, Gingered *Magnolia* Bark, Parched Puerariae Radix and Glycyrrhizae Radix, on Inhibition of Production of Advanced Glycation Endproducts The part (1) of this Example was repeated except that extract from each of Euphorbiae radix, gingered *Magnolia* bark, parched Puerariae radix and Glycyrrhizae radix was dissolved in 15% Tween80 and cultured for 90 days.

(3) Effect of Magnolol on Inhibition of Production of Advanced Glycation Endproducts Magnolol was dissolved in distilled water at concentrations of 3.33 μg/ml, 6.66 μg/ml, 13.32 μg/ml and 26.6 μg/ml, and then cultured for 37° C. for 30 days in the same manner as in the above part (1).

aminoguanidine, a positive control group, was tested in the same manner as in the above part (1) except that aminoguanidine was dissolved in distilled water at selected concentrations and cultured for 30 days and 90 days.

The test results are shown in FIGS. 1 to 8 and Table 1.

TABLE 1

| | | Inhibition (%) of production of advanced glycation endproducts | | |
|---|---|---|---|---|
| | | Concentration (μg/ml) | Inhibition (%) | IC$_{50}$ (μg/ml) |
| Herbal extract mixture (cultured for 30 days) | | 5 | 23.245 ± 0.698 | 18.12 |
| | | 10 | 44.998 ± 1.396 | |
| | | 25 | 63.548 ± 2.234 | |
| | | 50 | 93.283 ± 5.187 | |
| Euphorbiae radix extract (cultured for 90 days) | | 25 | 34.680 ± 2.685 | 32.07 |
| | | 50 | 56.456 ± 2.422 | |
| | | 100 | 64.260 ± 0.871 | |
| | | 200 | 93.376 ± 0.921 | |
| | | 250 | 96.853 ± 0.982 | |
| Gingered Magnolia bark extract (cultured for 90 days) | | 25 | 14.922 ± 5.040 | 27.80 |
| | | 50 | 94.135 ± 3.192 | |
| Parched Puerariae radix extract (cultured for 90 days) | | 25 | 25.155 ± 1.542 | 42.50 |
| | | 50 | 643.712 ± 3.069 | |
| | | 100 | 100 | |
| | | 200 | 100 | |
| | | 250 | 100 | |
| Glycyrrhizae radix extract (cultured for 90 days) | | 25 | 49.37 ± 1.802 | 28.40 |
| | | 50 | 62.262 ± 14.68 | |
| | | 100 | 100 | |
| | | 200 | 100 | |
| | | 250 | 100 | |
| Magnolol (cultured for 30 days) | | 3.33 | 36.36 ± 1.61 | 5.36 |
| | | 6.66 | 55.75 ± 2.11 | |
| | | 13.32 | 77.05 ± 1.70 | |
| | | 26.64 | 100 | |
| Aminoguanidine | Cultured for 30 days | 27.5 | 45.78 ± 2.400 | 34.90 |
| | | 55 | 55.43 ± 4.000 | |
| | | 110 | 73.52 ± 1.750 | |
| | | 550 | 96.41 ± 2.200 | |
| | Cultured for 90 days | 27.5 | 39.647 ± 3.406 | 30.80 |
| | | 55 | 65.712 ± 3.242 | |
| | | 110 | 65.714 ± 5.394 | |
| | | 55 | 89.873 ± 2.554 | |

As can be seen in Table 1, the herbal extract mixture of the present invention, when cultured for 30 days, showed a very low $IC_{50}$ of 18.12 μg/ml, indicating a very excellent effect on the inhibition of production of advanced glycation endproducts.

Meanwhile, the extract from each of Euphorbiae radix, gingered *Magnolia* bark, parched Puerariae radix and Glycyrrhizae radix, when cultured for 90 days, showed a low $IC_{50}$, indicating that it has an excellent effect on the inhibition of production of advanced glycation endproducts. However, when cultured for 30 days, the single herbal extract was not so excellent in its effect, suggesting that its effect will be shown upon long-term administration.

Furthermore, the inventive herbal extract mixture showed a much lower $IC_{50}$ than that of aminoguanidine, a positive control group, indicating that it has a very excellent effect on the inhibition of production of advanced glycation products.

Accordingly, it can be found that the single herbal extract according to the present invention has an inhibitory effect against the production of advanced glycation endproducts, and the inventive herbal extract mixture has a higher effect than that of the single herbal extract on the inhibition of production of advanced glycation endproducts.

Test Example 2

Effect of Inventive Herbal Extract Mixture on Treatment of Diabetic Complications In order to examine the effect of the inventive herbal extract mixture on the treatment of diabetic complications, the following tests were performed.

1. Test Animals

Four-week-old SD male rats weighing 120-140 g were housed in cages at one animal for each cage and allowed for access to general solid food and water while adapting the animals to an animal room of this institute (the applicant).

The animal room was maintained under the following conditions: temperature 23±3° C.; relative humidity: 50±10%; illumination time: 12 hours (a.m. 8 to p.m. 8); ventilation number: 10-20 times/hr; and illumination intensity: 150-300 Lux. During the test period, the temperature and humidity of the animal room were automatically controlled by a constant temperature and humidity chamber, and environmental conditions such as illumination intensity were regularly measured. Also, there was no change influencing the tests.

The test animals were divided into the following four groups: (1) a normal group administered with carboxymethyl cellulose (NC+CMC); (2) a diabetes-induced group administered with carboxymethylcellulose (DC+CMC); (3) a diabetes-induced group administered with the herbal extract mixture (DC+HMP); (4) and a diabetes-induced group administered with a positive control (Eparlestat) (DC+S11). The diabetes-induced groups each consisted of 9-10 animals, and the normal group consisted of 5-6 animals. The body weights of the animals were similar between the test groups.

2. Induction of Diabetic Complications by Streptozotocin

Streptozotocin (STZ) (N-(methylnitrosocarbamyl)-D-glucosamine), which is a chemical substance of breaking selectively β-cells to induce high blood glucose conditions by insulin deficiency, was used to induce diabetes. Particularly, single high dose streptozotocin (SHDS) can be seen to be suitable for a diabetic complication model since it irreversibly induces high blood glucose conditions by the mass necrosis of β-cells.

The test animals were adapted to the animal room and then fasted overnight. Streptozotocin was dissolved in 0.1 M citrate buffer (pH 4.5), and just then, injected into the abdominal cavities of the fasted animals at a dose of 60 mg/kg. At 2 days after administering the streptozotocin solution, tail vein blood was sampled from the animals and examined for blood glucose level. Rats having a blood glucose level of more than 300 mg/ml were determined to be diabetes-induced rats.

As a positive control group, Epalrestat (ON0-2235; referred to as "S11") which is currently used as an agent for treating diabetic complications was used.

(3) General Observation (Changes in Body Weight, and Food and Water Intakes)

To examine a therapeutic effect against chronic diabetic complications, the rats was continued to maintain in diabetic conditions for 30 days. From day 31, the rats were administered with the drugs for 8 weeks.

Since the herbal extract mixture (HMP) and Epalrestat (S11) used in the tests are insoluble in water, they were dissolved in 1% carboxymethylcellulose before use. The normal group was administered with carboxylmethylcellulose so as to eliminate an effect caused by carboxylmethylcellulose.

For the two diabetes-induced groups other than the normal group, each of 1 g/kg of the herbal extract mixture (HMP) and 25 mg/kg of Epalrestat (S11) was dissolved in 1% CMC and administered orally to the rats by a sonde daily for 8 weeks.

After administering the samples during the administration period, the test animals were fasted for at least 15 hours at one day before autopsy, and then measured for body weight.

The body weight was measured every day, the feed intake was measured one time a week, and the water intake was measured every day.

The measurement results are shown in Table 2 below.

TABLE 2

|  | Early stage (g) | End stage (g) | Increase in body weight (g) |
| --- | --- | --- | --- |
| NC + CMC | 209.26 ± 28.94 | 462.09 ± 32.91 | 252.83 |
| DC + CMC | 154.33 ± 27.26 | 220.50 ± 64.28 | 66.17 |
| DC + HMP | 153.50 ± 45.06 | 251.71 ± 40.01 | 98.21 |
| DC + S11 | 154.03 ± 45.46 | 283.24 ± 42.60 | 129.21 |

Note:
NC + CMC: normal group + carboxymethylcellulose
DC + CMC: diabetes-induced group + carboxymethylcellulose
DC + HMP: diabetes-induced group + herbal extract mixture
DC + S11: diabetes-induced group + positive control (Epalrestat)

As can be seen in Table 2, the body weight was increased by about 252.83 g for the normal group, and only 66.17 g for the diabetes-induced group administered with carboxymethylcellulose. Also, the body weight was increased by 98.21 g for the diabetes-induced group administered with the herbal extract mixture (HMP), and 129.21 g for the diabetes-induced group administered with Epalrestat (S11), a positive control. As such, an increase in the body weight of the group administered with the inventive herbal extract mixture was lower than that of the Epalrestat (S11)-administered group, but higher than that of the diabetes-induced group administered with carboxymethylcellulose.

Furthermore, in spite of low body weight, the diabetes-induced group administered with carboxylmethylcellulose consumed 2 times more feed than that of the normal group, and the positive control Epalrestat (S11)-administered group consumed more feed than that of the diabetes-induced group. However, the group administered with the inventive herbal extract mixture consumed slightly less feed than that of the diabetes-induced group, and the diabetes-induced group ingested 7 times more water than that of the normal group.

Also, the group administered with the herbal extract mixture ingested about 5 times less water than that of the diabetes-induced group, and the group administered with the positive control Epalrestat (S11) ingested more water than that of the diabetes-induced group.

(4) Measurement of Organ Weight

One day before autopsy, the test animals were fasted for at least 15 hours and then measured for body weight. Then, the animals were anesthetized with ethyl ether, from which blood was collected via the abdominal aorta. Some of the collected blood was treated with heparin, and some of whole blood was centrifuged at 3,000 rpm and 4° C. for 15 minutes. From each of the blood samples, plasma was isolated and stored at −80° C. before use in data analysis.

The kidneys of the animals were removed after washing by perfusion and measured for weight. Next, the kidneys were separated into cortex and medulla, which were rapidly cooled and stored at −80° C. In addition, the liver, lungs, pancreas, spleen and heart were separated and measured for weight.

The measurement results are shown in Table 3 below.

herbal extract mixture showed the similar effect to that of the positive control Epalrestat (S11).

5. Analysis of Biochemical Factors in Serum (1) Blood Glucose Lowering Effect

At two-week intervals up to before autopsy, blood was taken from the orbital veins and measured for plasma glucose level with a glucose kit. The plasma glucose level was measured at 500 nm UV by a glucose oxidase method.

(2) Improvement Effect on Kidney Function (a) Blood Urea Nitrogen (BUN)

BUN was determined by measuring absorbance at 580 nm by a urease-indophenol method.

(b) Triglyceride

Triglyceride content was quantified by measuring absorbance at 550 nm by an enzymatic method (POD).

(c) Total Cholesterol Level

Total cholesterol level was determined by measuring absorbance at 500 nm by an enzymatic method.

(d) Creatinine

Creatinine was determined by measuring absorbance at 515 nm by a modified Jaffe's method.

TABLE 3

|  |  | Heart | Liver | Spleen | Lungs | Kidneys | Pancreas |
| --- | --- | --- | --- | --- | --- | --- | --- |
| NC + CMC | Absolute Weight (g) | 1.64 ± 0.07 | 10.60 ± 0.72 | 0.79 ± 0.10 | 1.84 ± 0.23 | 2.65 ± 0.18 | 1.13 ± 0.21 |
|  | Relative weight (%) | 0.25 ± 0.02 | 2.30 ± 0.12 | 0.17 ± 0.02 | 0.40 ± 0.04 | 0.58 ± 0.04 | 0.25 ± 0.05 |
| DC + CMC | Absolute Weight (g) | 0.84 ± 0.18*** | 10.30 ± 1.99 | 0.46 ± 0.15*** | 1.44 ± 0.24** | 2.92 ± 0.45 | 0.79 ± 0.24** |
|  | Relative Weight (%) | 0.37 ± 0.06*** | 4.62 ± 0.71*** | 0.20 ± 0.03* | 0.65 ± 0.14*** | 1.35 ± 0.37*** | 0.35 ± 0.09** |
| DC + HMP | Absolute Weight (g) | 0.88 ± 0.14** | 10.71 ± 1.21 | 0.48 ± 0.10*** | 1.58 ± 0.21* | 2.95 ± 0.48 | 0.93 ± 0.14 |
|  | Relative Weight (%) | 0.35 ± 0.03*** | 4.31 ± 0.48*** | 0.19 ± 0.02 | 0.64 ± 0.08*** | 1.18 ± 0.10*** | 0.38 ± 0.07*** |
| DC + S11 | Absolute weight (g) | 0.95 ± 0.11 | 11.63 ± 1.08 | 0.54 ± 0.09 | 1.55 ± 0.13 | 3.18 ± 0.30 | 0.86 ± 0.11 |
|  | Relative Weight (%) | 0.34 ± 0.03*** | 4.15 ± 0.40*** | 0.19 ± 0.02 | 0.55 ± 0.06*** | 1.14 ± 0.11*** | 0.31 ± 0.05* |

Note:
NC + CMC: normal group + carboxymethylcellulose
DC + CMC: diabetes-induced group + carboxymethylcellulose
DC + HMP: diabetes-induced group + herbal extract mixture
DC + S11: diabetes-induced group + positive control (Epalrestat)
Statistical comparison with normal group:
*p < 0.05, p < 0.01, and
***p < 0.001.

As can be seen in Table 3, the diabetes-induced group showed an increase in the relative weight of all organs excluding the pancreas, as compared to the normal group, and particularly, it showed more than two times increase in the relative weights of the kidneys and liver. The group administered with the inventive herbal extract mixture showed a decrease in the weight of each organ as compared to that of the diabetes-induced group, but this decrease was not significant. Also, the (e) Protein Protein in serum was determined by BCA assay. Serum was reacted with a bicinchonicic acid solution of bicinchonicic acid, $Na_2CO_3$, $NaHCO_3$ and $C_4H_4O_6Na_2.2H_2O$ in 0.1N NaOH and a 4% $CuSO_4.5H_2O$ solution and then measured for absorbance at 562 nm.

The measurement results are given in Table 4 below.

TABLE 4

|  | Glucose level (mg/dl) | BUN (mg/dl) | Triglyceride (mg/dl) | Total cholesterol (mg/dl) | Creatinin (mg/dl) | Protein (µg/µl) |
| --- | --- | --- | --- | --- | --- | --- |
| NC + CMC | 124.93 ± 16.25 | 15.12 ± 0.54 | 33.38 ± 6.62 | 63.73 ± 11.05 | 1.54 ± 0.08 | 12.63 ± 0.28 |
| DC + CMC | 408.79 ± 63.10*** | 33.13 ± 5.13*** | 70.20 ± 13.14*** | 54.76 ± 11.85 | 1.75 ± 0.17* | 12.47 ± 0.42 |

TABLE 4-continued

|  | Glucose level (mg/dl) | BUN (mg/dl) | Triglyceride (mg/dl) | Total cholesterol (mg/dl) | Creatinin (mg/dl) | Protein (μg/μl) |
| --- | --- | --- | --- | --- | --- | --- |
| DC + HMP | 271.22 ± 72.28***## | 26.62 ± 3.51***# | 50.35 ± 16.63# | 53.56 ± 6.18 | 1.57 ± 0.28* | 12.35 ± 1.61* |
| DC + S11 | 197.94 ± 76.66*### | 23.60 ± 5.15***## | 46.18 ± 8.26*## | 59.50 ± 13.88 | 1.22 ± 0.16***## | 10.79 ± 0.85***# |

Note:
NC + CMC: normal group + carboxymethylcellulose
DC + CMC: diabetes-induced group + carboxymethylcellulose
DC + HMP: diabetes-induced group + herbal extract mixture
DC + S11: diabetes-induced group + positive control (Epalrestat)
Statistical comparison with normal group:
*$p < 0.05$,
**$p < 0.01$, and
***$p < 0.001$
Statistical comparison with diabetes-induced group:
$p < 0.05$,
$p < 0.01$, and
$p < 0.001$.

As can be seen in Table 4, the blood glucose levels were 408.79±63.10 mg/dl for the diabetes-induced group, and 271.22±72.28 mg/dl for the inventive herbal extract mixture-administered group, indicating that the inventive herbal extract mixture is excellent in the blood glucose-lowering-effect-as-compared to the diabetes-induced group ($p<0.01$). The group administered with the positive control Epalrestat showed a blood glucose level of 197.94 mg/dl.

Furthermore, the BUN level, an index of the kidney function, was about 2.4 times higher in the diabetes-induced group than in the normal group. The BUN level was significantly lower for the inventive herbal extract mixture-administered group than for the diabetes-induced group ($p<0.05$).

Moreover, the triglyceride level was much higher in the diabetes-induced group (70.20±13.14 mg/ml) than in the normal group (33.38±6.62 mg/dl) ($p<0.001$), and significantly lower in the inventive herbal extract mixture-administered group (50.35±16.63 mg/dl) than in the diabetes-induced group ($P<0.05$).

Also, the creatinine level was remarkably increased from 1.54±0.08 mg/dl to 1.75±0.17 mg/dl for the diabetes-induced group, and lowered to 1.57±0.28 mg/dl for the inventive herbal extract mixture administered group. Although the creatinine level is also used as an index of the kidney function, it is not a sensitive measure. Accordingly, even when glomerular filtration rate is reduced by more than 50%, the creatinine level remains in the normal range. In view of this characteristic, a creatinine level of 1.57±0.28 mg/dl for the inventive herbal extract mixture-administered group indicates a significant improvement in the kidney function. As shown in Table 3 above, the administration of the inventive herbal extract mixture resulted in a reduction in the kidney hyprotrophy as compared to the diabetes-induced group, indicating an improvement in the kidney function.

Accordingly, it can be found that the inventive herbal extract mixture-administered group showed not only a reduction in the kidney hypertrophy but also remarkable reductions in the BUN, triglyceride and creatinine levels, as compared to the diabetes-induced group, suggesting a significant improvement in the kidney function.

(6) Anti-Cataract Effect

From the eyeballs removed under a microscope, the eye lenses were separated and transferred onto 24-well plates each containing 2 ml of a saline solution. Then, the eye lenses were photographed with a digital camera. The opacity of the eye lenses was analyzed by the use of an imaging system program.

The eye lenses were photographed with a camera and measured for weight. Then, the eye lenses were placed in phosphate buffer (pH 6.9) and homogenized at 4° C. For use in the measurement of enzymatic activity, some of the homogenized solution was centrifuged at 3,000 rpm for 20 minutes, and the supernatant was collected and stored at −80° C. For use in the measurement of content of sorbitol, etc., the remaining homogenized solution was added with $ZnSO_4$ and NaOH so as to remove protein, and centrifuged at 3,000 rpm for 20 minutes, and the supernatant was collected and stored at −80° C.

Figure 1:
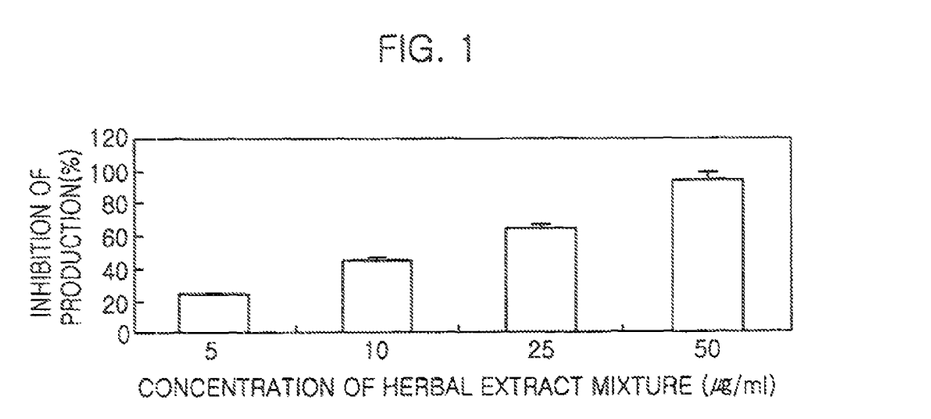
FIG. 1 shows graphically the effect of the inventive herbal extract mixture on the inhibition of production of advanced glycation endproducts.
Figure 2:
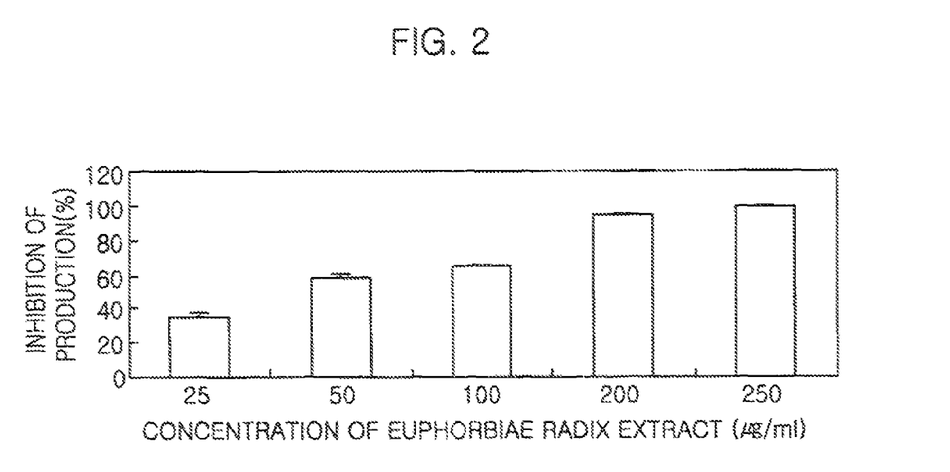
FIG. 2 shows graphically the effect of the inventive Euphorbiae radix extract on the inhibition of production of advanced glycation endproducts.
Figure 3:
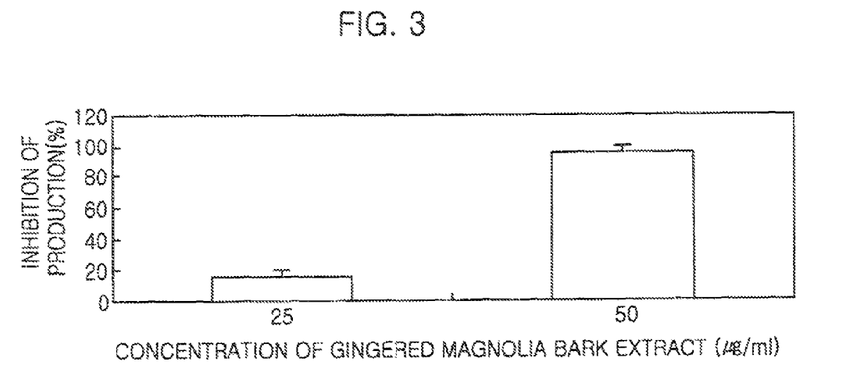
FIG. 3 shows graphically the effect of the inventive gingered *Magnolia* bark extract on the inhibition of production of advanced glycation endproducts.
Figure 4:
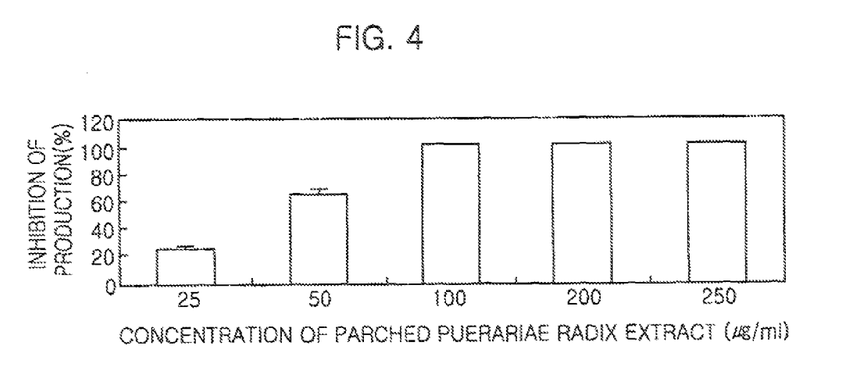
FIG. 4 shows graphically the effect of the inventive parched Puerariae Radix extract against the production of advanced glycation endproducts.
Figure 5:
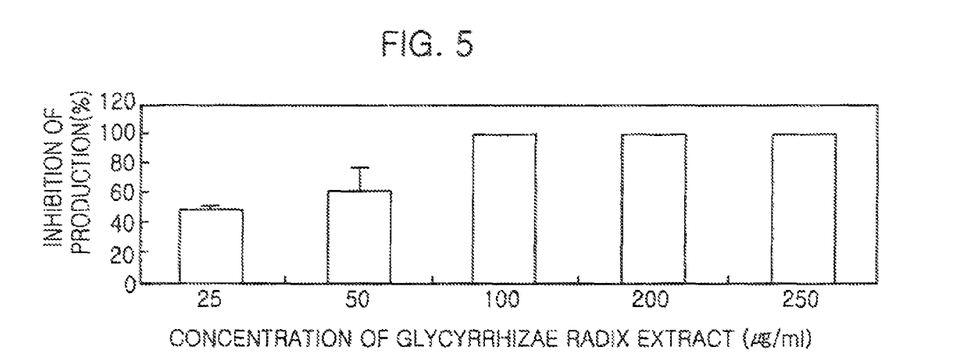
FIG. 5 shows graphically the inhibitory effect of the inventive Glycyrrhizae radix extract on the inhibition of production of advanced glycation endproducts.
Figure 6:
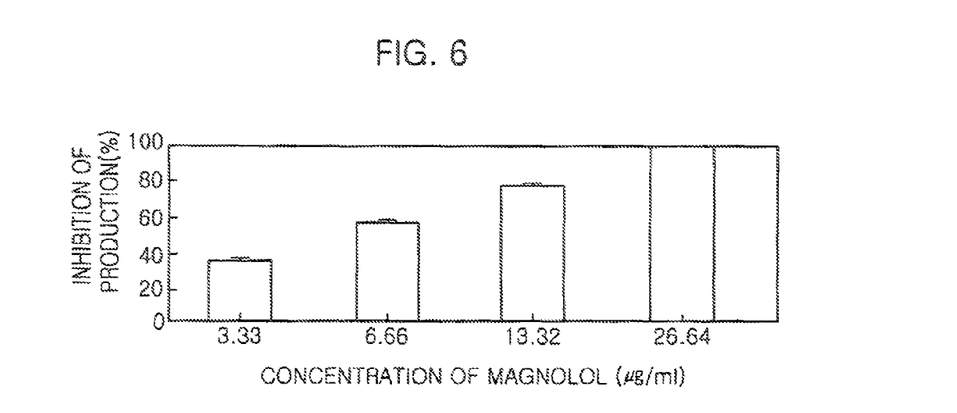
FIG. 6 shows graphically the effect of the inventive magnolol on the inhibition of production of advanced glycation endproducts.
Figure 7:
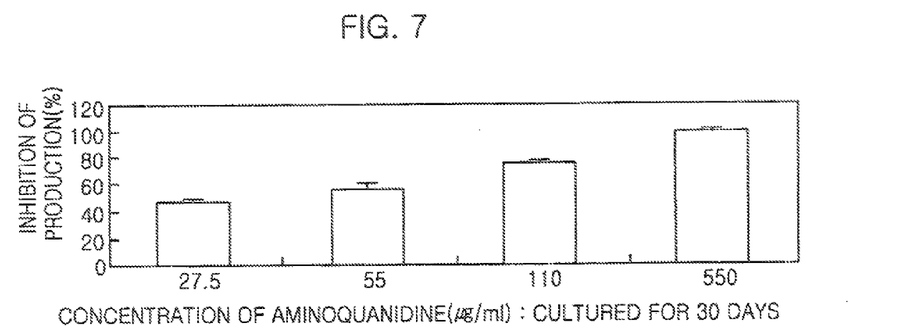
FIG. 7 shows graphically the effect of aminoguanidine (cultured for 30 days) on the inhibition of production of advanced glycation endproducts.
Figure 8:
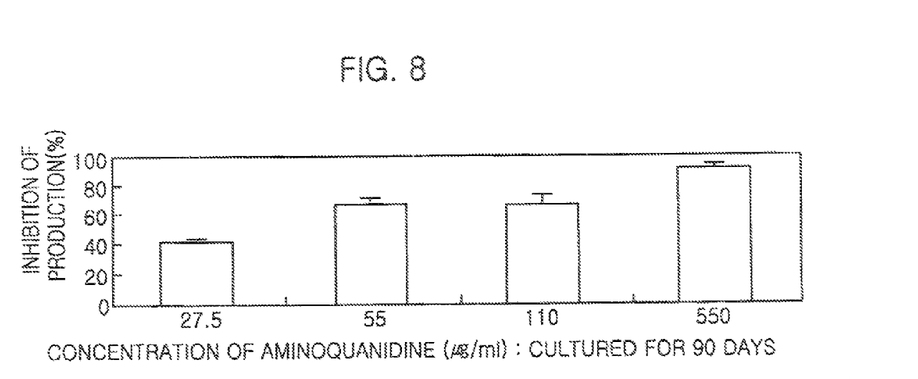
FIG. 8 shows graphically the effect of aminoguanidine (cultured for 90 days) on the inhibition of production of advanced glycation endproducts.
Figure 9:
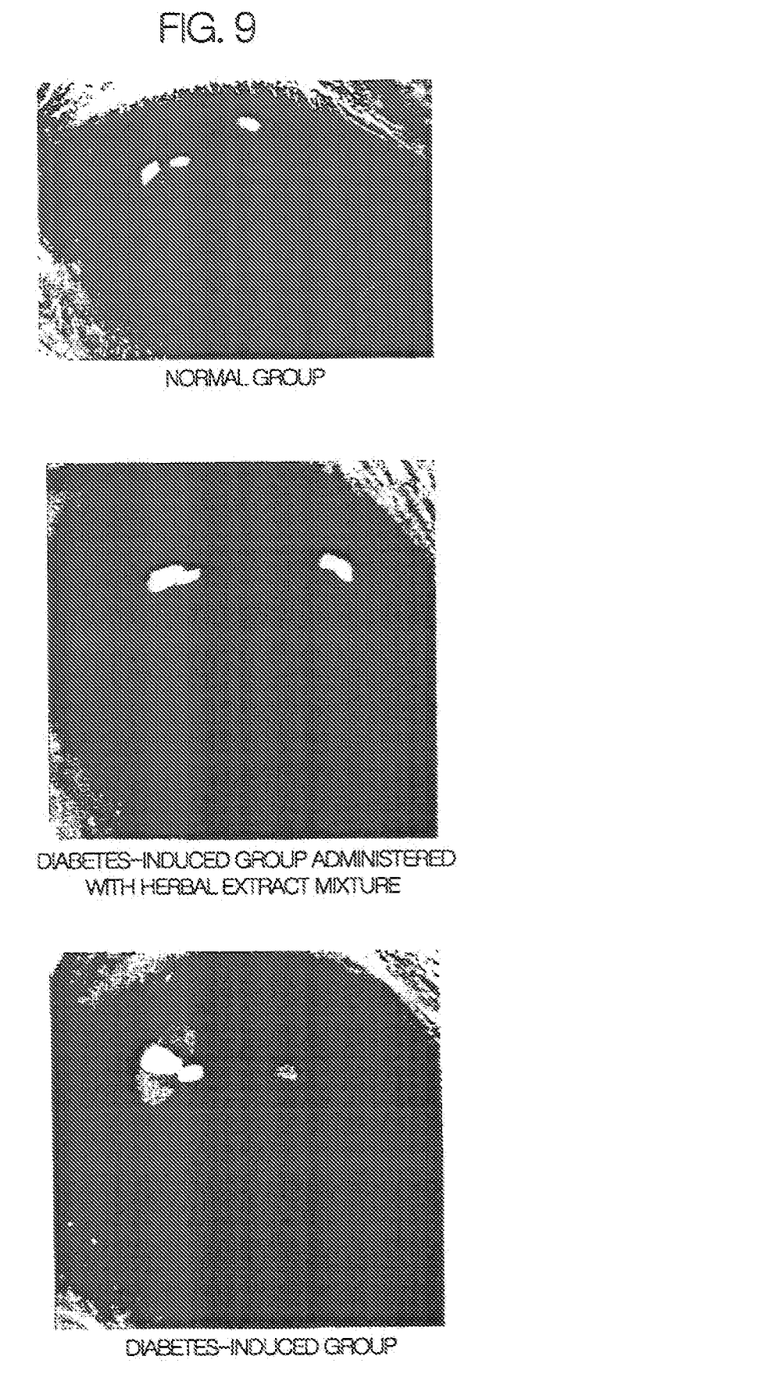
FIG. 9 depicts photographs showing the eyeballs of test rats observed in test examples of the present invention.
Figure 10:
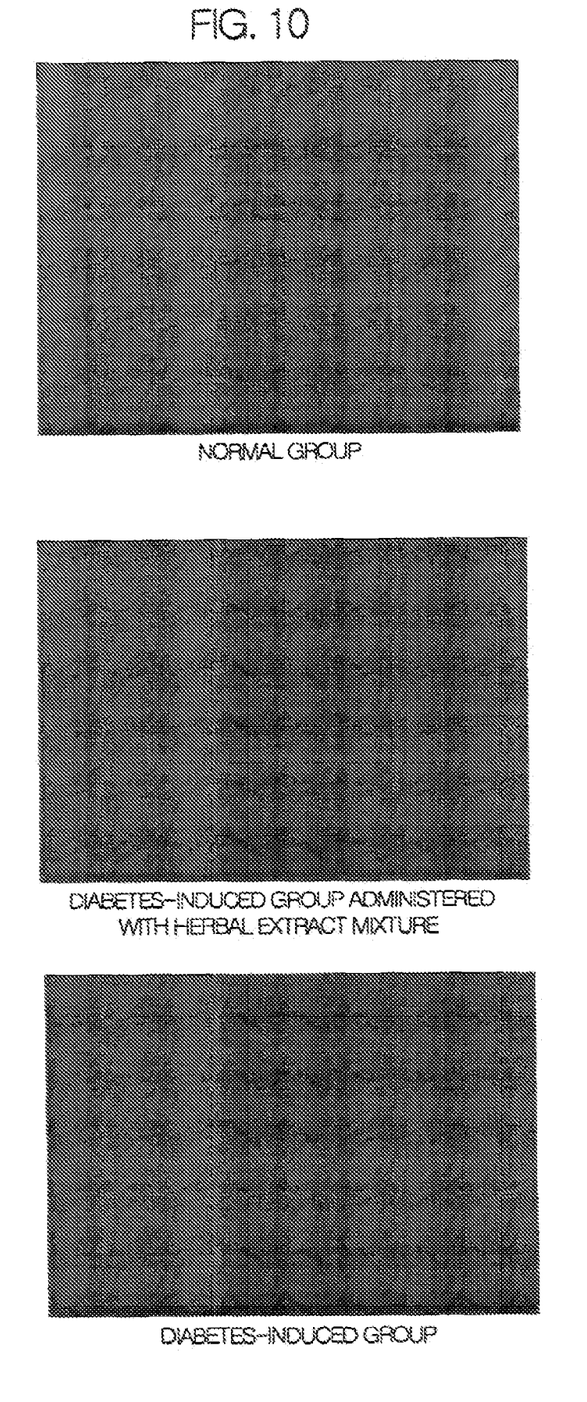
FIG. 10 depicts photographs showing the eye lenses of test rats observed in test examples of the present invention.

The results of visual observation for the eyeballs are shown in FIG. 9, and the results of camera observation for the eye lenses are shown in FIG. 10. Also, the opacity of the eye lenses is shown in Table 5 below.

TABLE 5

|  | Eye lens's opacity (20 pixels/m²) | Eye lens's opacity (%) |
| --- | --- | --- |
| NC | 39.91 ± 23.36 | 8.31 ± 5.21 |
| DC | 200.53 ± 47.88 | 66.84 ± 14.89*** |
| DC + HMP | 136.54 ± 73.52 | 37.20 ± 20.25**## |
| DC + S11 | 134.04 ± 45.00 | 37.38 ± 13.56***### |

Note:
NC: normal group
DC: diabetes-induced group
DC + HMP: diabetes-induced group + herbal extract mixture
DC + S11: diabetes-induced group + positive control (Epalrestat)
Statistical comparison with normal group:
*$p < 0.05$,
**$p < 0.01$, and
***$p < 0.001$
Statistical comparison with diabetes-induced group:
$p < 0.05$,
$p < 0.01$, and
$p < 0.001$.

As shown in FIG. 9 and Table 10, the diabetes-induced group started to show cataract from 6 weeks after inducing diabetes. Regarding the eyeball conditions of all the groups on the day of autopsy, the eyeballs of three of seven animals in the diabetes-induced group were covered in white, and one animal showed very weak symptoms. In the case of the group administered with the positive control Epalrestat (S11), both eyeballs of four of seven animals were covered in while, and one animal showed weak symptoms in the right eyeball. The reason why as many as five animals in the positive control Epalrestat (S11)-administered group showed cataract symptoms is believed to be because rats subjected to Streptozocin induction two times were as many as two animals. It is generally known that when Streptozocin induction is performed two times, an increase in body weight will be low and the eye lens opacity becomes severe. Also, in the case of the inventive herbal extract mixture-administered group, three of seven animals showed cataract symptoms in both eyeballs.

As can be seen in Table 5, the mean opacity of the eye lenses was 8.31±5.21% for the normal group, and 66.84±14.89%, indicating that the eye lens opacity was severe. Also, the positive control Epalrestat (S11) and the inventive herbal extract mixture were administered to the diabetes-induced groups, respectively, they significantly reduced the cataract symptoms to 37.38±13.56% (p<0.001) and 37.20±20.25% (p<0.01), respectively.

Figure 11:
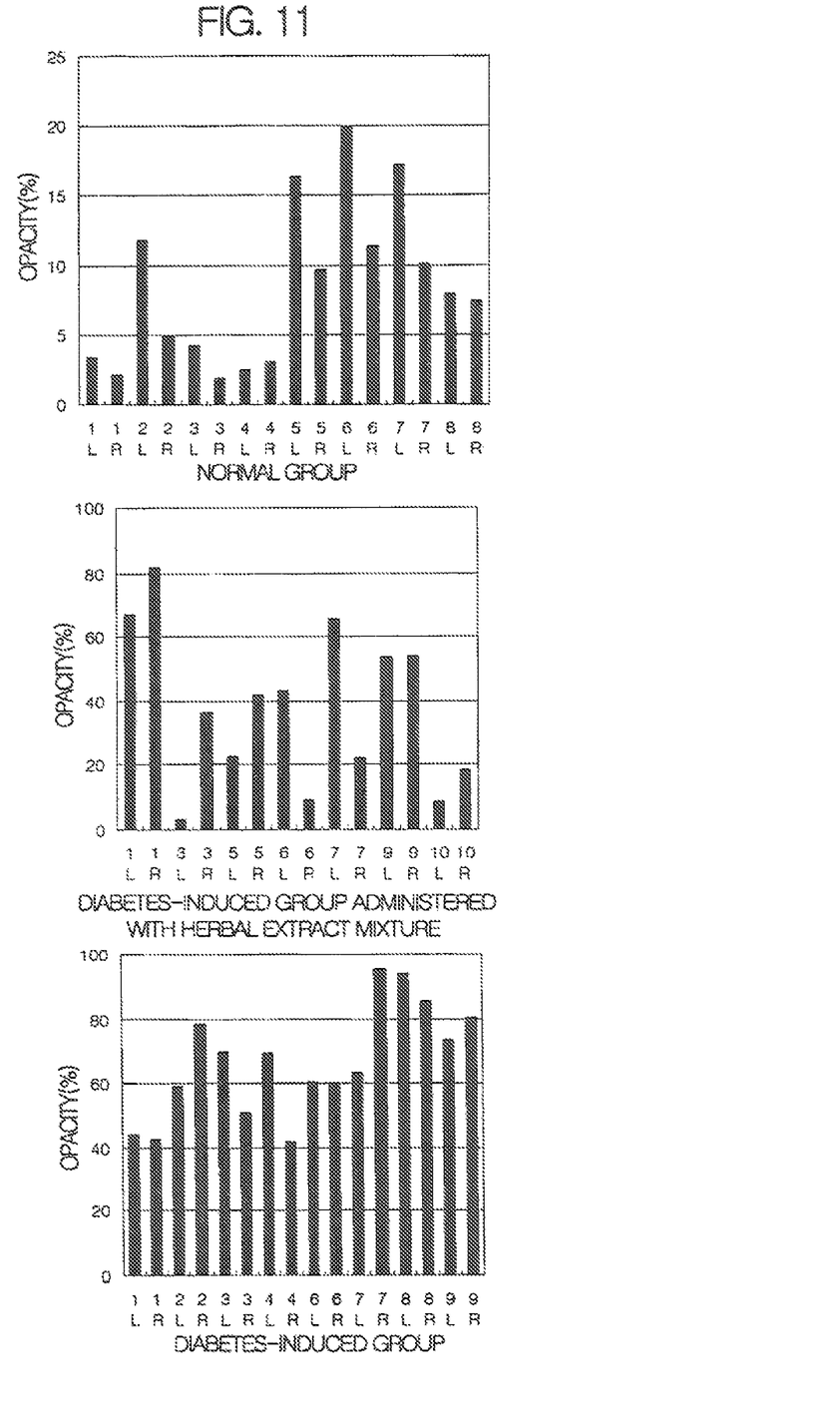
FIG. 11 shows graphically the opacity of the eye lenses of test rats measured in test examples of the present invention.

Also, as shown in FIG. 11 wherein reference numerals 1, 2, 3 . . . , denotes the number of rats, and L or R denotes the right or left eye lens of rats, the eye lenses of the normal group showed an opacity of about 20% and were also clear in appearance. An opacity of about 20% can be seen as normal. The animals of the diabetes-induced group all showed an eye lens opacity of more than 40% and mostly showed an eye lens opacity of more than 60%. Also, rats showing an eye lens opacity of more than 80% were 3 in number. However, the animals of the inventive herbal extract mixture-administered group mostly showed an eye lens opacity of about 40%. Among these rats, rats showing a normal level of the eye lens opacity also existed and rats showing an eye lens opacity of more than 60% were 2 in number.

Accordingly, it can be found that the inventive herbal extract mixture will be effectively used for the prevention and treatment cataract symptoms caused by chronic diabetes.

Test Example 3

Test of Acute Toxicity in Oral Administration to Rats

To examine the acute toxicity of the inventive herbal extract mixture, the following tests were performed.

Acute toxicity test was conducted on six-week-old specific pathogen-free (SPF) SD rats as test animals. The herbal extract mixture prepared in Example above was suspended in water and administered orally to each test animal group consisting of 2 animals, at a dose of 6 g/kg/15 ml one time. After administering the test substance, the animals were observed for death, clinical symptoms and body weight change, and subjected to hematological examination and hematobiochemical examination. After autopsy, the animals were visually observed for abnormalities in abdominal and thoracic organs.

As a result, there were no special clinical symptoms in all the animals administered with the test substance. Also, there was no dead animal, and in view of the results of the body weight measurement, hematological examination, hematobiochemical examination, etc., a change in toxicity was not observed.

The above results demonstrated that the inventive herbal extract mixture is a safe substance which does not show a change in toxicity up to a dose of 6 g/kg and has a minimum lethal dose ($LD_{50}$) for oral administration of at least 6 g/kg.

Formulation 1: Preparation of Tablets 100.0 mg of each of the medicinal herbal extract prepared in Examples 1-3, 90.0 mg of corn starch, 175.0 mg of lactose, 15.0 mg of L-hydroxypropylcellulose, 905.0 mg of polyvinylpyrrolidone and a suitable amount of ethanol were uniformly mixed and granulized by a wet granulation method. The granules were added with 1.8 mg of magnesium stearate and tableted in such a manner that one tablet weighed 400 mg.

Formulation 2: Preparation of Capsules 100.0 mg of each of the medicinal herbal extracts prepared in Examples 1-3, 80.0 mg of corn starch, 175.0 mg of lactose and 1.8 mg of magnesium stearate were uniformly mixed, and filled in capsules at an amount of 360 mg for each capsule.

Formulation 3: Preparation of Functional Drinks

Drinks were prepared with the following composition by a conventional method:

| | |
|---|---|
| Horney | 522 mg |
| Thioctic acid amide | 5 mg |
| Nicotinic acid amide | 10 mg |
| Sodium riboflavin hydrochloride | 3 mg |
| Pyridoxine hydrochloride | 2 mg |
| Inositol | 30 mg |
| Orotic acid | 50 mg |
| Herbal extract of the invention | 500 mg |
| Water | 200 mg. |

INDUSTRIAL APPLICABILITY

As described above, the inventive single herbal extract, mixed herbal extract or magnolol inhibits the production of advanced glycation endproducts causing diabetic complications, at a much lower concentration than that of aminoguanidine, a positive control group. Particularly, the herbal extract mixture is excellent in a blood glucose-lowering effect, prevents a reduction in body weight, and induces not only a reduction in kidney hypertrophy but also significant reductions in BUN, triglyceride and creatinine levels, etc., thus inhibiting the deterioration of kidney functions. Also, the herbal extract mixture remarkably reduces the opacity of the eye lens. Accordingly, the herbal extract mixture can be applied in pharmaceutical compositions and functional foods for the prevention and treatment of diabetic complications caused by the production of advanced glycation endproducts, including diabetic retinopathy, diabetic cataract, diabetic nephropathy and diabetic neuropathy.

Also, the inventive herbal extract reduces the incidence of oxidative stress as a result of the inhibition of production of advanced glycation endproducts. Thus, the inventive herbal extract can be applied in pharmaceutical compositions and functional foods for the prevention and delay of aging caused by oxidative stress.

What is claimed is:

1. A method for treating diabetic complications comprising administering an extract which comprises Euphorbiae radix, gingered *Magnolia* bark, parched Puerariae radix and Glycyrrhizae radix, wherein the weight ratio of the Euphorbiae radix, the gingered *Magnolia* bark, the parched Puerariae radix and the Glycyrrhizae radix is 1:1:1:1.

2. The method for treating diabetic complications according to claim 1, wherein the extract is obtained by: crushing and drying each of Euphorbiae radix, gingered *Magnolia* bark, parched Puerariae radix and Glycyrrhizae radix; mixing the crushed herbal materials together; extracting the dried herbal material with alcohol or aqueous alcohol solution; filtering the extract; and concentrating the filtrate under reduced pressure.

3. The method for treating diabetic complications according to claim 1, wherein the diabetic complication is selected from diabetic retinopathy, diabetic cataract, diabetic nephropathy and diabetic neuropathy.

* * * * *